United States Patent [19]

Ohtsuki et al.

[11] Patent Number: 5,010,528
[45] Date of Patent: Apr. 23, 1991

[54] DOPPLER FLOW VELOCITY DISTRIBUTION MEASURING APPARATUS

[76] Inventors: Shigeo Ohtsuki, 11-7 Chiyoda 4-chome, Sagamihara-shi, Kanagawa 229; Motonao Tanaka, 4-16 Kunimi 4-chome, Sendai-shi, Miyagi 981, both of Japan

[21] Appl. No.: 465,183

[22] PCT Filed: Jun. 30, 1989

[86] PCT No.: PCT/JP89/00659
§ 371 Date: Feb. 28, 1990
§ 102(e) Date: Feb. 28, 1990

[87] PCT Pub. No.: WO90/00033
PCT Pub. Date: Jan. 11, 1990

[30] Foreign Application Priority Data

Jun. 30, 1988 [JP] Japan .................. 63-164573

[51] Int. Cl.$^5$ .................. G01S 15/00; G01F 1/66; A61B 8/06
[52] U.S. Cl. .................. 367/90; 73/861.25; 128/661.09
[58] Field of Search .................. 73/861.38, 861.25; 128/661.09; 367/90

[56] References Cited

U.S. PATENT DOCUMENTS

| 4,744,367 | 5/1988 | Kodone et al. | 73/861.25 |
| 4,759,375 | 7/1988 | Namekawa | 128/661.09 |
| 4,790,322 | 12/1988 | Iiuuma | 73/861.25 |

FOREIGN PATENT DOCUMENTS 226044 of 1987 European Pat. Off. .
WO85/05454 of 1985 World Int. Prop. O. .

Primary Examiner—Ian J. Lobo
Attorney, Agent, or Firm—Dickstein, Shapiro & Morin

[57] ABSTRACT

An apparatus for measuring the velocity distribution in a fluid by a pulse-Doppler method using an ultrasonic waver or an electromagnetic wave. The observation wave is transmitted to and received from the fluid and the reflected echo from the fluid is received so as to obtain the Doppler frequency. A predetermined transverse section is scanned with the observation wave so as to obtain the Doppler velocity distribution in the transverse section. Since the Doppler velocity distribution only contains the component in the direction of the observation wave, the Doppler velocity distribution is cumulatively integrated in the direction orthogonal to the direction of the observation wave and the integrated values are differentiated again in the direction of the observation wave, thereby obtaining the component in the orthogonal direction by calculation. If the observation wave is an ultrasonic beam, it is possible to observe the velocity distribution of the bloodstream in the heart.

4 Claims, 6 Drawing Sheets $u_1 = (u_1^+) + (u_1^-)$ $u_2 = (u_2^+) + (u_2^-)$

DOPPLER FLOW VELOCITY DISTRIBUTION MEASURING APPARATUS

Technical Field

The present invention relates to a Doppler flow velocity measuring apparatus and, more particularly, to a Doppler flow velocity measuring apparatus which is capable of obtaining the two-dimensional velocity distribution of a fluid on a predetermined transverse section by one beam scanning of said transverse section.

Background Art

A Doppler velocity measuring apparatus for obtaining the flow of a fluid or the movement of a moving member in an object being examined by utilizing a Doppler effect is known. By this apparatus, an ultrasonic or electromagnetic wave, especially, a pulsating burst wave is transmitted to the object being examined, and a reflected echo is obtained at each point in the direction of the beam so as to utilize a Doppler effect. This method is widely utilized as a pulse-Doppler method.

Such a velocity measurement method is useful for knowing the flow velocity vector distribution in a predetermined transverse section being observed which is composed of a plane or a curved surface by scanning the transverse section with the transmitted beam. This method is very useful for knowing the movement of clouds by using an electromagnetic wave, and the bloodstream velocity distribution in the heart of the body by using an ultrasonic wave. Especially, in the latter case, it is possible to observe the bloodstream distribution without invasion and produce excellent results on the diagnosis of the function of the heart and the like.

As is well known, according to this kind of pulse-Doppler method, since the frequency of a received signal deviates depending upon the movement of a reflecting member, the velocity distribution of a fluid along each point of the an ultrasonic beam is obtained from the deviated frequency (Doppler frequency) obtained by comparison between the frequencies of the transmitted signal and the received signal. The pulse-Doppler method, however, suffers from the serious problem that the velocity information obtained from the pulse-Doppler method only provides a velocity component in the direction of a beam.

Therefore, even if two-dimensional velocity distribution information is obtained by moving the pulse beam along a predetermined transverse section by the mechanical movement of a probe or electronic linear or sector scanning, since the information obtained only contains the component in the direction of the beam, the velocity and the acceleration distribution in the displayed image obtained from the information and the pressure distribution in the closed region obtained from the velocity information of each pixel contain a large innegligible error.

In order to obtain a component in a direction different from the direction of a beam in the transverse section plane scanned with the beam, a method of obtaining the correlation of the data in the directions of adjacent beams is conventionally investigated. However, such calculation of the correlation makes the apparatus complicated and since the processing speed is lowered, the amount of data observable per unit time is reduced.

The present inventors proposed a method of using an advective accelerating component of a fluid in order to infer the velocity component data in a direction different from the direction of an ultrasonic wave, the direction orthogonal thereto in ordinary case, in Japanese Patent Application Nos. 236919/1987 and 236920/1987.

According to the above-described related art, a plurality of burst waves are transmitted from an ultrasonic probe to a fluid at a predetermined recurrence period, the echo obtained from the fluid is received by the ultrasonic probe and the flow velocity component data (hereinunder referred to as "Doppler velocity") at each point in the direction of the beam is obtained from the received signal every moment by utilizing the above-described Doppler effect.

The Doppler velocities obtained are sequentially stored in a memory, and the points which satisfy the conditions for obtaining the advective acceleration component are obtained from the thus-stored two-dimensional information. At the points which satisfy the conditions, the advective acceleration component is calculated and at the other points, the advective acceleration component is obtained by interpolation.

The flow velocity component in a direction different from the direction of the beam is obtained from both the thus-obtained advective acceleration component and the stored Doppler velocity distribution.

DISCLOSURE OF INVENTION

However, even in the above-described velocity distribution measuring apparatus adopting a Doppler method using an advective acceleration velocity, the arithmetic operation is complicated as in the other systems, and it is impossible to solve the problem of the increase in the size of the apparatus and a long measuring time.

Accordingly, it is an object of the present invention to eliminate the above-described problems in the prior art and to provide an improved velocity distribution measuring apparatus adopting a Doppler method which is capable of obtaining a velocity component in a direction different from the direction of a beam by a simple arithmetic operation and at a high speed.

To achieve this aim, the present invention is characterized in that after the Doppler velocity in the direction of an ultrasonic or electromagnetic beam is obtained by the transmitted and received waves of the beam, a component in a direction different from the direction of the beam is obtained from the Doppler velocity data through an integration step and a differentiation step which is obtained along the transverse section being observed.

More specifically, the Doppler velocity distribution obtained as two-dimensional information is first stored in a first memory. The stored Doppler velocity data are then sequentially read out in a direction different from the direction of the ultrasonic wave, the direction orthogonal thereto, in an ordinary case, accumulated in the direction of readout, and the contents of the data are stored in a second memory for the respective pixels.

In the present invention, the value obtained from accumulation, namely, the accumulated value at each pixel in the direction in which the data are read out coincides a value known as a stream function, as will be obvious from the later explanation.

In the present invention, all the stream functions are further stored two-dimensionally along the transverse section and then differentiated in the direction of the beam.

The present inventors have found that the thus-differentiated value of each pixel constitutes a velocity component in a direction different from the direction of the beam, for example, the direction orthogonal thereto and is useful for the measurement of the flow velocity distribution, as is clear from the following detailed explanation.

The Doppler velocity often has a three-dimensional expanse in the actual object being examined. In this case, since the cumulatively integrated Doppler velocity has a component in the direction vertical to the beam scanning plane, compensating calculation is preferably executed when a stream function is obtained in order to compensate this component. The present invention enables further accurate velocity distribution measurement by the compensating calculation.

According to the present invention, the thus-measured two-dimensional components enable the calculation of the velocity distribution along a predetermined transverse section being observed, the acceleration distribution and the pressure in the closed region, etc.

According to the present invention, the Doppler velocities of a fluid in the direction of an ultrasonic or electromagnetic beam is obtained from the beam which is used for linear or sector scanning in the same way as in the prior art, and the thus-obtained Doppler velocities are stored in a first memory.

The Doppler velocities are then read out in a direction different from the direction of the beam, and the cumulatively integrated value at each pixel is obtained by cumulative integration of the Doppler velocities in the direction of readout, and is stored in a second memory as a cumulatively integrated value distribution.

The cumulatively integrated value distribution represents the stream function in the fluid.

According to the present invention, the stream functions are again sequentially differentiated in the direction of the ultrasonic beam and are stored in a third memory as a differential value distribution, which represents a Doppler velocity component in the direction of readout.

Consequently, it is possible to measure the true Doppler velocity at each pixel from the component in the direction of the beam stored in the first memory and the component in the direction of readout stored in the third memory. The Doppler vector is visually displayed on a two-dimensional colored screen or the like, and it is possible to know the acceleration distribution and the pressure distribution in the closed region, if necessary.

It goes without saying that the results of observation in accordance with the present invention are utilized for not only the observation of a distribution in the form of an image display but also for various analyses in the form of numerical information.

According to the present invention, it is also preferable to use not only the observed Doppler velocity component in the direction of the beam but also the data obtained by inferring and removing the component in the direction orthogonal to the scanning plane from the Doppler velocity component. Such compensating calculation is possible from various data on the object being examined. For example, in the case of observing a bloodstream in the heart, the compensation is obtained from the calculation of the model conditions inferred from the pressure at each part of the heart, the shape of the heart, etc.

Figure 1:
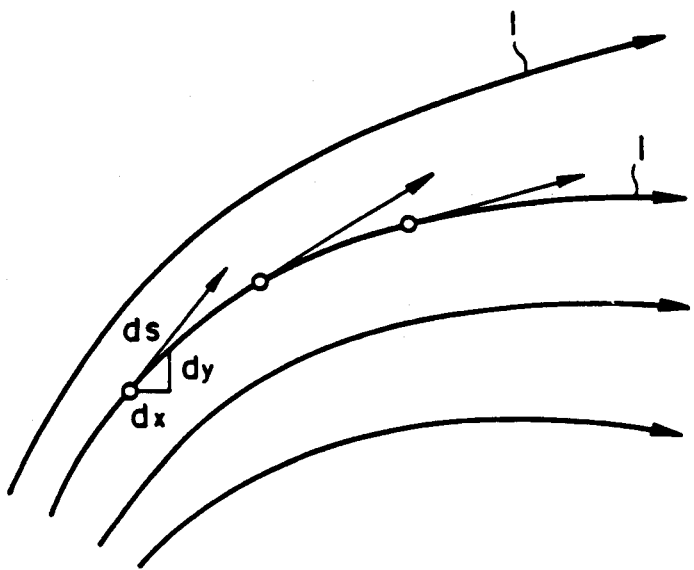
FIG. 1 is an explanatory view of a stream function in the flow field to which the present invention is applied.

Best Mode for Carrying Out the Invention

Preferred embodiments of the present invention will be explained hereinunder with reference to the accompanying drawings.

Principle of Invention

The equation of motion with respect to a general flow will first be explained with reference to FIG. 1.

In order to visibly catch the flow field at a certain moment, a streamline is utilized. Generally, when the directions of all tangents to a curve in a flow field agree with the direction of a streamline vector with respect to the curve at every point on the curve, this curve is called a streamline, which is represented by the reference numeral 1 in FIG. 1.

For example, when a large amount of aluminum powder dispersed on the surface of a closed channel stream is photographed with a slow shutter speed, the movement of the aluminum powder comes out as short lines on the film and a multiplicity of lines connecting those short lines come out as the streamlines 1 shown in FIG. 1. Although the streamline 1 is temporally constant in a steady flow, the shape of the streamline 1 changes at every moment in an unsteady flow, so that it is possible to visually observe the flow in a predetermined region by seeing the change of the streamline.

It is possible to analyze the flow field by the equation of motion on the basis of the streamline, and a function important for this analysis is known as a stream function.

That is, when a certain function S (x, y) has the following relationship, this function is called a stream function:

$$\frac{\partial S}{\partial x} = -v \qquad \frac{\partial S}{\partial y} = u \qquad (1)$$

The stream function represented by the equation (1) is a stream function in a two-dimensional stream. In the present invention, the flow can be sufficiently measured by such two-dimensional analysis. It goes without saying that processing of a three-dimensional stream enables more accurate measurement in the actual measurement of bloodstream or the like, and this will be described later.

The symbols u and v represent the velocity component in the direction of a beam and the velocity component in the direction orthogonal thereto, respectively, in a two-dimensional stream measured by a pulse-Doppler method.

The direction of a beam is a direction of the y-axis with the direction of the x-axis orthogonal thereto. The fundamental principle of the present invention is to obtain the unknown component v.

The relationship between the stream function S (x, y) and the streamline will be explained in the following by using the components u and v.

When the stream function S (x, y) is constant, if the function is totally differentiated, the following equation holds:

$$dS = \frac{\partial S}{\partial x} dx + \frac{\partial S}{\partial y} dy = 0 \quad (2)$$

This relationship satisfies the continuous equation in two dimensions.

When the relationship represented by the equation (1) is substituted into the equation (2), the following equation holds:

$$-vdx + udy = 0 \quad \ldots (3)$$

That is, $$\frac{dy}{dx} = \frac{v}{u} \quad (4)$$

This means that the direction sx/dy of a tangent to a line in which S (x,y) is constant agrees with the direction of the streamline 1 shown in FIG. 1 in which the x component is u and the y component is v.

In other words, it is evident that the locus of points in which the stream function is constant is a streamline and that the relationships represented by the equations (1) to (4) constantly hold in a two-dimensional stream.

From the above analysis it is clear that since the Doppler velocity obtained by an ultrasonic pulse-Doppler method is a velocity component u in the direction of the x-axis, it is possible to obtain the stream function S (x, y) by integrating the Doppler velocity component u in the direction of the y-axis which is orthogonal to the direction of the beam (x-axis) from the right-hand term in the equation (1).

It is also evident that if the thus-obtained stream function S (x, y) is then differentiated again in the direction of the x-axis, which is the direction of the beam, the x component v in the direction orthogonal to the x-axis is obtained from the equation (1).

Figure 2:
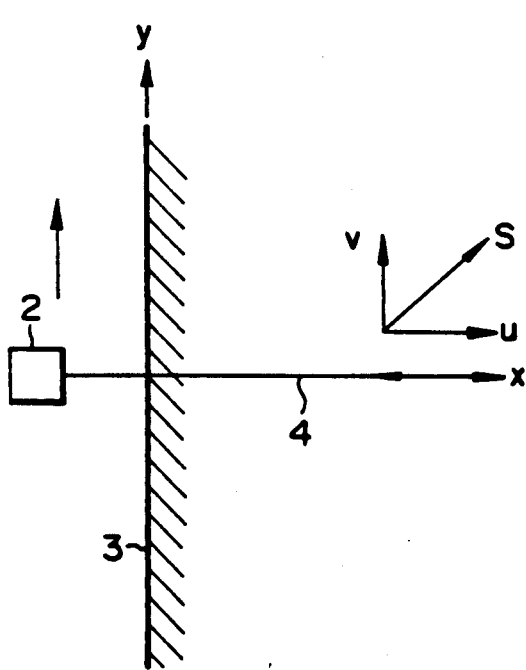
FIG. 2 is an explanatory view of the relationship between the measured value and the stream function obtained from the linear scanning of an object being examined with an ultrasonic beam which is transmitted to and received from the object.

FIG. 2 schematically shows the Doppler velocity detecting operation of a Doppler velocity measuring apparatus according to the present invention.

In FIG. 2, when an ultrasonic probe 2 transmits an ultrasonic beam 4 to a fluid, for example, an object 3 being examined and the reflected echo is detected, the Doppler velocity data u in the direction of the ultrasonic beam 4 in the fluid 3 is obtained from a change in the frequency. It will be understood that if it is assumed that the direction of the beam is the x-axis, the direction agrees with the direction in the flow field shown in FIG. 1.

Actually, the probe 2 scans in the direction orthogonal to the direction of the beam x, namely, in the direction of the y-axis, and the Doppler velocity u, which is a component obtained by the ultrasonic beam 4 is data at each pixel on a two-dimensional transverse section.

It will therefore be understood that the velocity data v in the direction orthogonal to the ultrasonic beam 4 can be obtained as the velocity data v in the orthogonal direction from the direction of the tangent to the streamline 1 shown in FIG. 1 and the Doppler velocity data u by obtaining the stream function S of the streamline 1 shown in FIG. 1.

The equation (1) already defines:

$$\frac{\partial S}{\partial y} = u \quad (5)$$

When the equation (5) is integrated with respect to y, $$S(x,y) = \int_{-\infty}^{y} u(x,y) dy \quad (6)$$

and the stream function (x, y) is obtained.

It is therefore possible to obtain the streamline 1 shown in FIG. 1 by displaying the data on the predetermined values of the stream function S (x, y), thereby detecting the velocity data v in the direction orthogonal to the ultrasonic beam 4 in the above-described way.

In the present invention, in the actual operation process of the equations (5) and (6), the cumulative integration represented by the equation (6) is carried out in the direction of the y-axis. Since the component u, namely, the Doppler velocity has already been obtained, mere cumulative integration of this component in the y-axis, which is orthogonal to the direction x of the beam produces the accumulated value at each pixel, namely, the stream function. By differentiating the stream function obtained at each pixel again in the direction of the beam, namely, in the direction of the x-axis, the component v in the orthogonal direction, namely, in the direction of y is obtained.

As described above, it will be understood that if only a two-dimensional flow field is considered in FIG. 2, it is possible to obtain the component v by first obtaining the stream function of the two-dimensional field by cumulatively integrating the component u, which is the Doppler velocity, in a direction different from the direction of the component u and then differentiating the stream function in the direction of the beam, namely, along the x-axis.

The principle of obtaining a component in a direction different from the ultrasonic beam from the Doppler velocity distribution in the direction of the ultrasonic beam is as described above. It will be understood that such two dimensions are obtained as two-dimensional data in the direction of an ultrasonic beam and the direction orthogonal thereto by a linear scanning of an ultrasonic probe by linear scanning and as the components in the direction of the ultrasonic beam and the direction in contact therewith by electronic sector scanning. Thus, desired velocity measurement is enabled both in linear and sector scanning.

Stream Function in Polar Coordinates

In FIG. 2, the ultrasonic probe 2 mechanically or electronically and linearly scans in the direction of the y-axis and, as a result, the flow field is represented by the x,y rectangular coordinates. In the present invention, it is naturally possible to execute the analysis using the stream function in polar coordinates.

Especially in the case of observing the bloodstream in the heart, the sector scanning of an ultrasonic beam is often utilized. In order to analyze the Doppler velocity obtained by such sector scanning, it is convenient to represent the Doppler velocity in polar coordinates with the position of the ultrasonic probe as the origin, as shown in FIG. 3.

Figure 3:
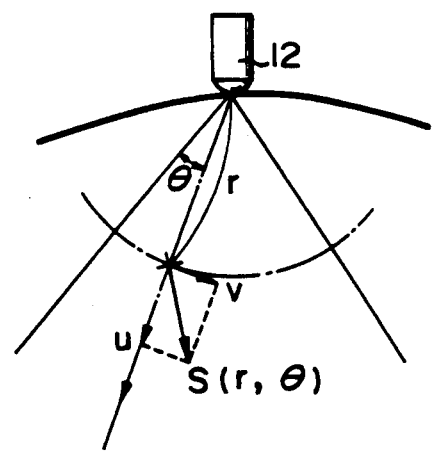
FIG. 3 is an explanatory view of a stream function in the polar coordinates in the case of applying the present invention to the sector scanning in an ultrasonic diagnostic apparatus.

In FIG. 3, polar coordinates are supposed to have the beam transmitting point of a vibrator 12 as the origin. In the polar coordinates, it is assumed that the stream function of a two-dimensional stream is S (r, $\theta$), the velocity components at the point (r, $\theta$) are (u, v), and the following relationship holds:

$$\frac{\partial S}{\partial r} = -v \quad (7)$$

$$\frac{\partial S}{r\partial \theta} = u \quad (8)$$

This relationship is the same as that represented by the equation (1) in the rectangular coordinates, and satisfies the continuous equation in two dimensions. That is, $$\frac{\partial u}{\partial r} + \frac{u}{r} + \frac{\partial v}{r\partial \theta} = 0 \quad (9)$$

If the equation (9) is totally differentiated on the assumption that S (x, y) is constant, $$\frac{rd\theta}{dr} = \frac{v}{u} \quad (10)$$

This equation indicates that the line connecting the points of the stream function at the same level is a streamline.

The stream function is obtained by integrating the equation (8) and is represented by the following equation:

$$S(r, \theta) = r\int u d\theta \quad \ldots (11)$$

In this way, it is also possible to obtain a component in a direction different from the direction of the ultrasonic beam from the Doppler velocity obtained by sector scanning by the analysis of polar coordinates in a similar processing to that of the rectangular coordinates.

More specifically, the Doppler velocity signal obtained by sector scanning only contains the component in the direction of the ultrasonic beam. This component for one frame on the transverse section is first stored in the memory.

The Doppler velocities at the respective points are read out in a direction different from the direction of the beam, namely, in the direction of a readout line along the arc which is equidistant from the beam origin by r, and are cumulatively integrated.

As a result, the cumulatively integrated value represents the stream function in the same way as in the case of the rectangular coordinates, as is clear from the equation (11).

The stream function distribution is differentiated again in the direction of the beam, thereby enabling the component along the arc which is equidistant from the beam origin to be obtained.

Example of Sector Scanning

It is obvious from the above explanation that the present invention is applicable to both linear scanning and sector scanning An embodiment of the present invention which is applied to an ultrasonic diagnostic apparatus will be explained with reference to the example shown in FIG. 4.

Figure 4:
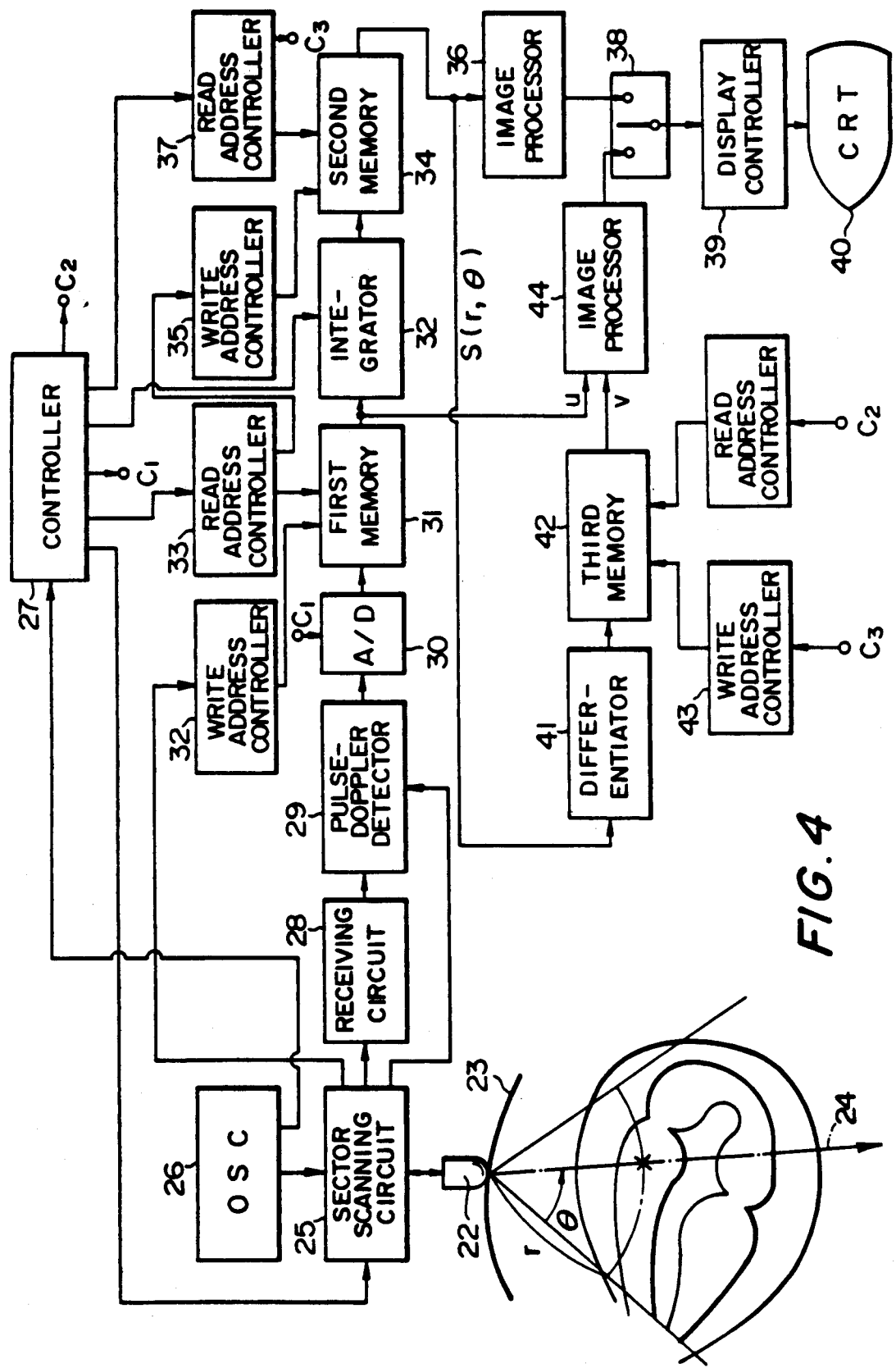
FIG. 4 is a block circuit diagram of a preferred embodiment of a Doppler velocity measuring apparatus according to the present invention which is applied to a sector scanning ultrasonic diagnostic apparatus.

In FIG. 4, an ultrasonic probe 22 is brought into close contact with the surface of an object 23 being examined. In this embodiment, the bloodstream distribution in the heart is observed. The probe 22 in this embodiment is composed of an electronic sector probe and transmits a sector beam 24 to the heart in accordance with an oscillation signal from a sector scanning circuit 25, as shown in FIG. 4.

As is well known, the pulse burst frequency of the ultrasonic beam is controlled by the oscillation signal obtained from an oscillator 26.

The output of the oscillator 26 is further supplied to a controller 27 to provide the controller 27 with a synchronous clock signal for controlling the entire ultrasonic diagnostic apparatus.

The controller 27 therefore drives the sector scanning circuit 25 in accordance with the control signal and controls the probe 22 so as to transmit the sector ultrasonic beam at a predetermined timing and to electronically scan a predetermined sector range with the beam.

The echo reflected from each part of the heart, which is the object being examined, is electrically received by the probe 22 and is transmitted from the sector scanning circuit 25 to the receiving circuit 28. The receiving circuit 28 determines the direction of reception in accordance with the transmitted beam 24, and separates the received signals depending upon the frequency so as to take out only the signals necessary for Doppler deviation. As is well known, the receiving circuit 28 is provided with at least a high pass filter for the above-described selection, and removes the signals from the heart wall and other tissues which slowly change while selectively taking out the signals from the bloodstream which quickly changes, thereby enabling the removal of the signals having a large intensity from the heart wall.

The thus-received signals are supplied to a pulse-Doppler detector 29 and detected after they are mixed with the transmitting frequency suppled from the sector scanning circuit 25. The pulse-Doppler detector 29 outputs a Doppler displacement signal, namely, Doppler velocity.

The detected Doppler velocities are converted into digital signals by an A/D converter 30 and sequentially stored in a first memory 31. In this embodiment, the first memory 31 is composed of a two-dimensional memory such as an image frame memory, and has a capacity for storing at least one sector scanning frame. The writing operation of the first memory 31 is controlled by an address control signal output from a write address controller 32 which is synchronously controlled by the sector scanning circuit 25. Data is written at a pixel corresponding to the depth (r) of the reflected echo and the scanning angle (θ).

In this way, the bloodstream velocity component u in the direction of the ultrasonic beam 24 for one scanning frame is stored in the first memory 31, and by using the component u, the component v is calculated in accordance with the present invention.

In the present invention, if the first memory has a capacity for at least three scanning frames, while the component v is calculated, the next sector scanning is executed, which is stored in a vacant memory, thereby enabling signal processing at real time by alternately storing the component u and reading the component u for the calculation of the component v.

The contents of the first memory 31 are sequentially read out along the arc having the same radius r, as is obvious from the above explanation, and are cumulatively integrated by the integrator 32.

The reading operation of the first memory 31 is preferably so controlled by a read address controller 33 as to be executed in accordance with the instruction from the controller 27 and in association with the scanning of the next frame by the sector scanning circuit 25.

The integrator 32 sequentially cumulatively integrates the input data and supplies the integrated values to a second memory 34 composed of an image frame memory so as to store the integrated values at predetermined positions. The writing operation of the second memory 34 is controlled by a write address controller 35 synchronously with the read address controller 33 which controls the reading operation from the first memory 31 in the direction of readout along the arc.

In this way, the distribution of the stream function S (r, θ) at each point of the scanning plane of the transverse section is stored in the second memory 34.

Figure 5:
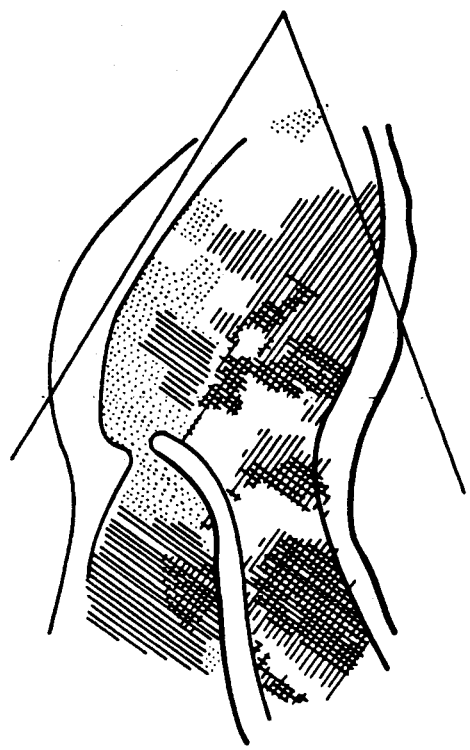
FIGS. 5 to 9 are explanatory views of the state in which the bloodstream distribution in the heart shown in FIG. 4 is measured.

FIG. 5 shows the displayed image of the Doppler velocity distribution stored in the first memory 31. As is obvious from FIG. 5, the Doppler velocity is represented by light and shade. The velocity increases with the degree to which the shade becomes darker.

The image shown in FIG. 5 is a conventional image of Doppler bloodstream distribution. Since the component in the direction of the ultrasonic beam solely is taken into consideration in this image, as described above, a great deal of skill is required for inferring the actual bloodstream.

Figure 6:
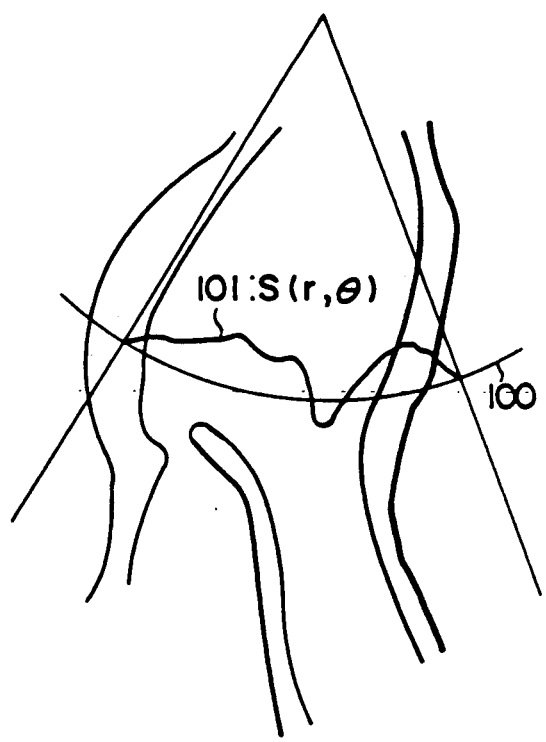

The present invention is characterized in that the integrator 32 cumulatively integrates the Doppler velocity shown in FIG. 5 in the direction of readout along the arc. The reference numeral 100 in FIG. 6 represents one readout line and the cumulatively integrated values along the readout line 100 are represented by the curve 101.

Figure 7:
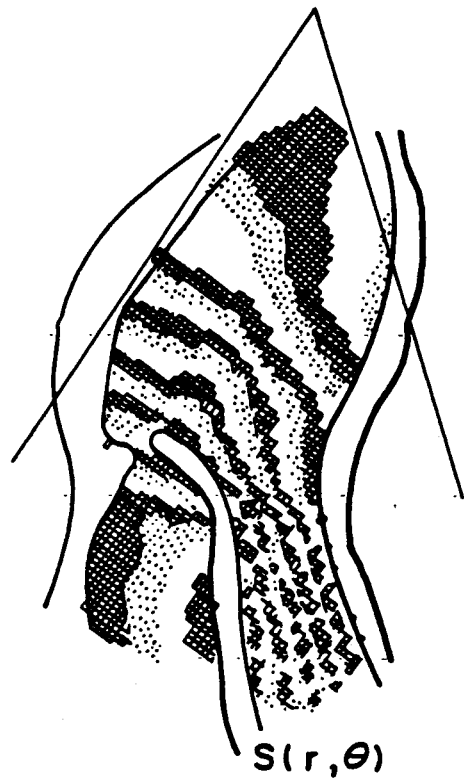

As is clear from the above explanation, the curve 101 is the stream function S (r, θ), and the result of the cumulative integration of the stream function S (r, θ) over the entire scanning region is shown as a displayed image in FIG. 7.

As is clear from FIG. 7, the image distinctly shows the direction of flow of the bloodstream in the heart. The image shown in FIG. 7 is obtained by processing the data in the second memory 34 by an image processor 36, as shown in FIG. 4. The data in the second memory 34 is supplied to the image processor 36 by the read address controller 37 under the control of the controller 27.

The image processor 36 normalizes the stream function data and converts the data into analog data which are supplied from a switch 38 to a CRT 40 for display through a display controller 39 as color image signals.

The switch 38 changes over between the stream function display and the flow vector diagram and is composed of contact devices manually or automatically switched.

The display controller 39 includes a color display circuit in this embodiment, and is capable of displaying the stream functions as a multiple-color image at real time.

The stream function S (r, θ) is read out of the second memory 34, as described above, and sequentially differentiated by a differentiator 41. The differentiating operation is carried out in order to obtain the component v in the direction of the arc. For this purpose, the read address controller 37 so controls that the contents of the second memory 34 are again read out in the direction of the beam, and the differentiation operation is sequentially carried out in the direction of readout.

Figure 8:
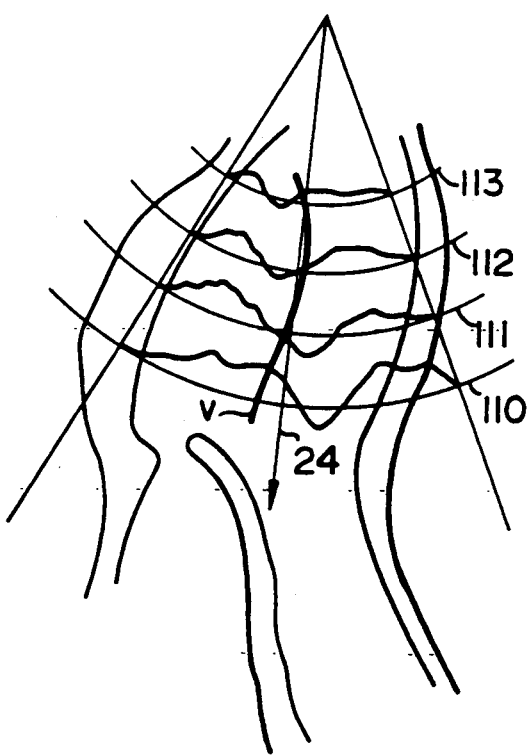

FIG. 8 shows the differentiating operation. A plurality of stream functions 110 to 113 shown in FIG. 8 are sequentially differentiated in the direction of the beam 24 so as to obtain the arc components v, which are sequentially stored in a third memory 42.

The storing operation of the third memory 42 is controlled by a write address controller 43. In this embodiment, since the writing operation is controlled in association with the data reading operation of the second memory 34, a synchronous signal $C_3$ is supplied from the read address controller 37 to the input of the write address controller 43.

When the arc components v for one frame are stored in the third memory 42, the arc components v and the components u in the direction of the beam stored in the first memory 31 are supplied to an image processor 44 and converted into predetermined image signals.

Figure 9:
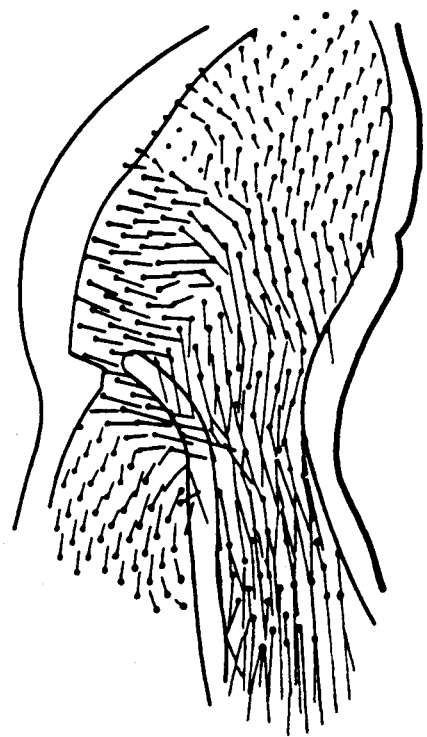

These signals are supplied to the display controller 39 through the switch 38, and are displayed as a flow vector diagram, for example, as the image of a synthesized vector of the components u and v, as shown in FIG. 9 in the same way as in the case of displaying the stream functions.

Thus, according to the present invention, it is possible to obtain a component in a direction different from the beam axis which is impossible in the prior art, thereby enabling the velocity measurement with high accuracy.

Stream function of three-dimensional stream

In the above explanation, it is assumed that the stream being observed is a two-dimensional stream, but in most cases, an object of measurement is a three-dimensional stream, as described above simply. For example, the bloodstream in the heart exhibits complicated three-dimensional motion.

The continuous equation in three dimensions is represented by the following equation:

$$\frac{\partial u}{\partial x} + \frac{\partial v}{\partial y} + \frac{\partial w}{\partial z} = 0 \tag{12}$$

The component w which is orthogonal to the plane scanned with an ultrasonic beam is included, and due to the influence of this component, an error still remains in the analysis of a two-dimensional stream.

Actually, processing a flow as a two-dimensional stream results in sufficient signal processing, but in the following embodiment, the orthogonal component w is further compensated.

The improvement according to the present invention in which the component w is inferred from another component such as the component u will be described in the following.

The principle of the improvement is based on the following standpoint. For example, a component u on the transverse section is a quantity which fundamentally three-dimensionally diverges, so that the component u has a divergent component on not only the x-y plane but also the x-z plane. If a divergent component, for example, $u_2$ an unknown component w cancel out each other, it is possible to remove the unknown component w by a residual component $u_1$ which is obtained by subtracting the x-z plane component $u_2$ from the measured component u.

Figure 10:
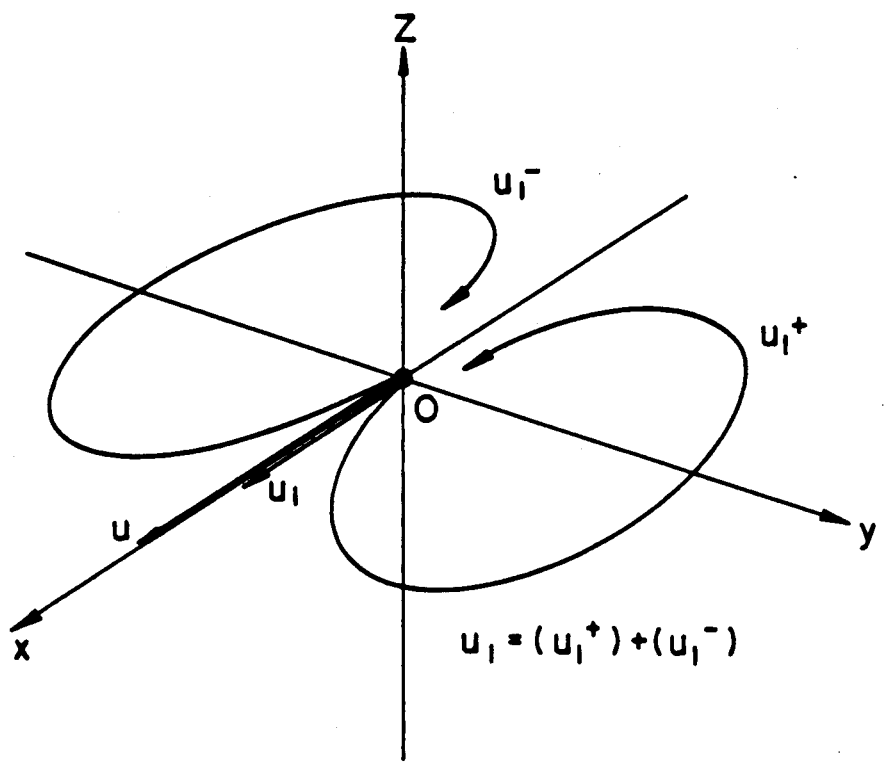
FIGS. 10 and 11 are explanatory views of the principle of measurement in the present invention in a three-dimensional stream.

FIG. 10 shows the component u observed at the point O of x, y, z three-dimensional coordinates. Since the component u diverges three-dimensionally, as described above, this can be represented by the x-y plane and the x-z plane. In FIG. 10, only the x-y plane is analyzed to simplify explanation.

It is naturally considered that a stream constantly returns like a vortex. The measured component u draws a vortex on the x-y plane as the component $u_1$ which is obtained by subtracting the component $u_2$ for cancelling out the later-described component w from the measured component u. In FIG. 10, the u component forms a return vortex $u_{1+}$ on the positive side of the x-y plane and a return vortex $u_{1-}$ on the negative side of the x-y plane.

Therefore, the component $u_1$ is represented as follows:

$$u_1 = (u_{1+}) + (u_{1-})$$

Figure 11:
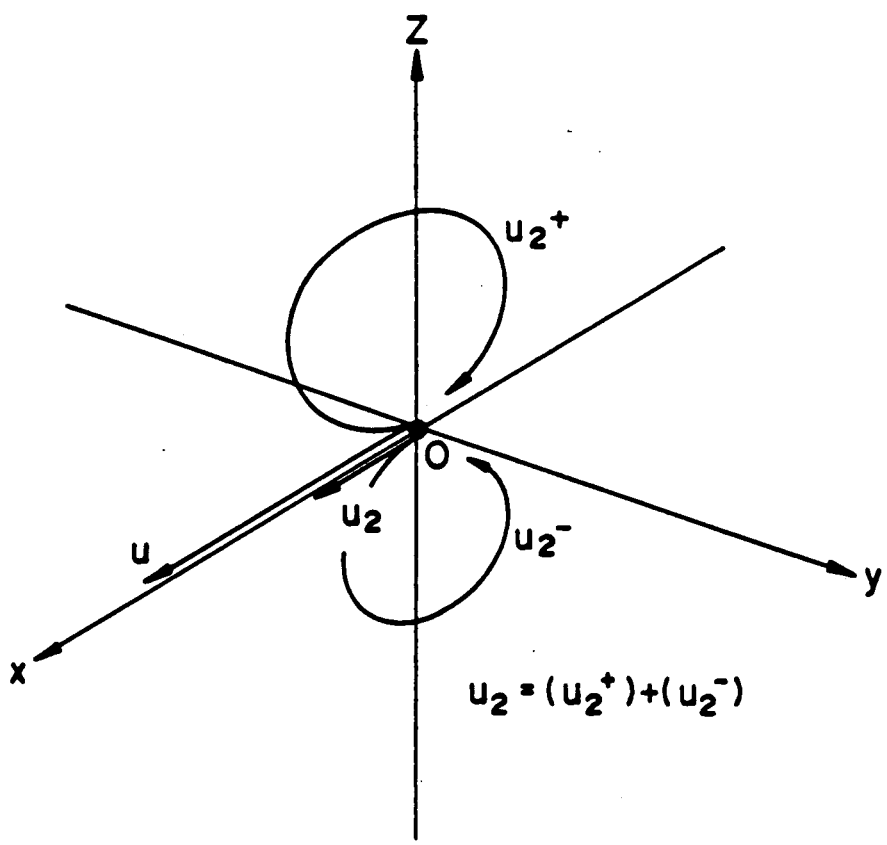

Similarly, FIG. 11 shows the component $u_2$ on the x-z plane which diverges at the point O. The component $u_2$ is similarly represented as follows:

$$u_2 = (u_{2+}) + (u_{1-})$$

What is important in the principle of this embodiment is that it is considered that the flow velocity component $u_2$ on the x-z plane of a fluid which flows into the point O agrees with the velocity component in the direction of w. Therefore, if the component $u_2$ is removed, it is possible to remove the error due to the component w without measuring the velocity in the direction of w.

It will therefore be understood that the equation (12) is represented by the following equation.

$$\frac{\partial u_1}{\partial x} + \frac{\partial u_2}{\partial x} + \frac{\partial v}{\partial y} + \frac{\partial w}{z} = 0 \quad (13)$$

In the equation (13), since the component $u_2$ and the component w cancel out each other, if $u_2$ is determined so that the following equation holds:

$$\frac{\partial u_2}{\partial x} + \frac{\partial w}{\partial z} = 0 \quad (14)$$

the continuous equation in three dimensions is represented by the following equation:

$$\frac{\partial u_1}{\partial x} + \frac{\partial v}{\partial y} = 0 \quad (15)$$

Thus, it will be understood that the flow can also be processed by the equation for a two-dimensional stream in this embodiment.

In this embodiment, only the Doppler velocity component distribution $u_1$ is cumulatively integrated after the component $u_2$ which corresponds to the component w obtained from the received signal by the probe, namely, the component u with the known conditions, for example, in the case of the measurement of the bloodstream in the heart, the size of the heart, the position of a valve, the blood pressure, etc. taken into consideration is subtracted from the measured value u.

Figure 12:
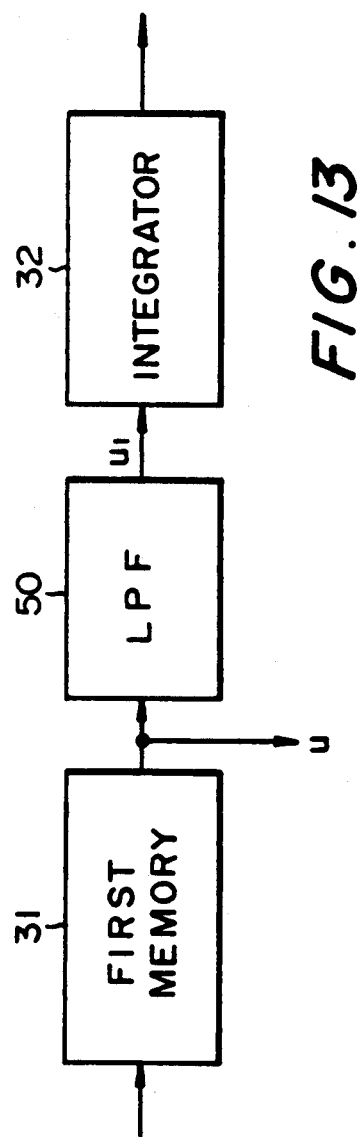
FIGS. 12 and 13 are block diagrams of the main parts of preferred embodiments of the present invention in a three-dimensional stream.

FIG. 12 shows an example of cumulative integration in a three-dimensional stream in accordance with the present invention. The cumulative integration shown in FIG. 12 is characterized in that when the Doppler velocity information stored in the first memory 31 is read out in a direction different from the direction of the beam, the information is supplied to the integrator 32 through a three-dimensional compensation circuit 50.

The Doppler velocity data u stored in the first memory and read out in a direction different from the direction of the beam, for example, the direction orthogonal thereto contains the component w in the direction of the z-axis, as described above. This component is the component $u_2$. The three-dimensional compensation circuit 50 is fundamentally composed of a low pass filter so as to remove the component $u_2$.

As is clear from FIG. 11, the direction in which the memory data for cumulative integration are read out is the direction of the y-axis, and the component $u_2$ for cancelling out the component w in the direction of the y-axis exists on the x-z plane. As a result, most of the spatial frequency components read out in the direction of the y-axis belong to a high-frequency region.

Therefore, the components $u_2$ to be removed are only high-frequency components in the data on principle, so that provision of a low pass filter at the precedent step to the integrator 32 enables the component $u_2$ to be removed to a substantially practical level. It is therefore possible to take out only the compensated component $u_1$ from the three-dimensional compensation circuit 50 composed of a low pass filter and, as a result, the cumulative integration is carried out with respect to the effective component $u_1$ solely with the error removed therefrom. Thus, highly accurate measurement is enabled with respect to a three-dimensional fluid.

In the present invention, the three-dimensional compensation circuit 50 is not restricted to a mere low pass filter. More complete elimination is enabled by discriminating between a plurality of spatial frequency components of the data read out of the first memory 31 in the orthogonal direction, connecting the outputs of discrimination to the corresponding low pass filters, and synthesizing the outputs obtained from the plurality of low pass filters.

That is, in the single low pass filter shown in FIG. 12, it is assumed that the component $u_2$ to be removed in FIG. 11 is a single return vortex. Actually, a plurality of return vortices exist on the x-z plane, and the sizes of these vortices are preferably discriminated so as to process the vortices separately from each other depending upon the size.

Figure 13:
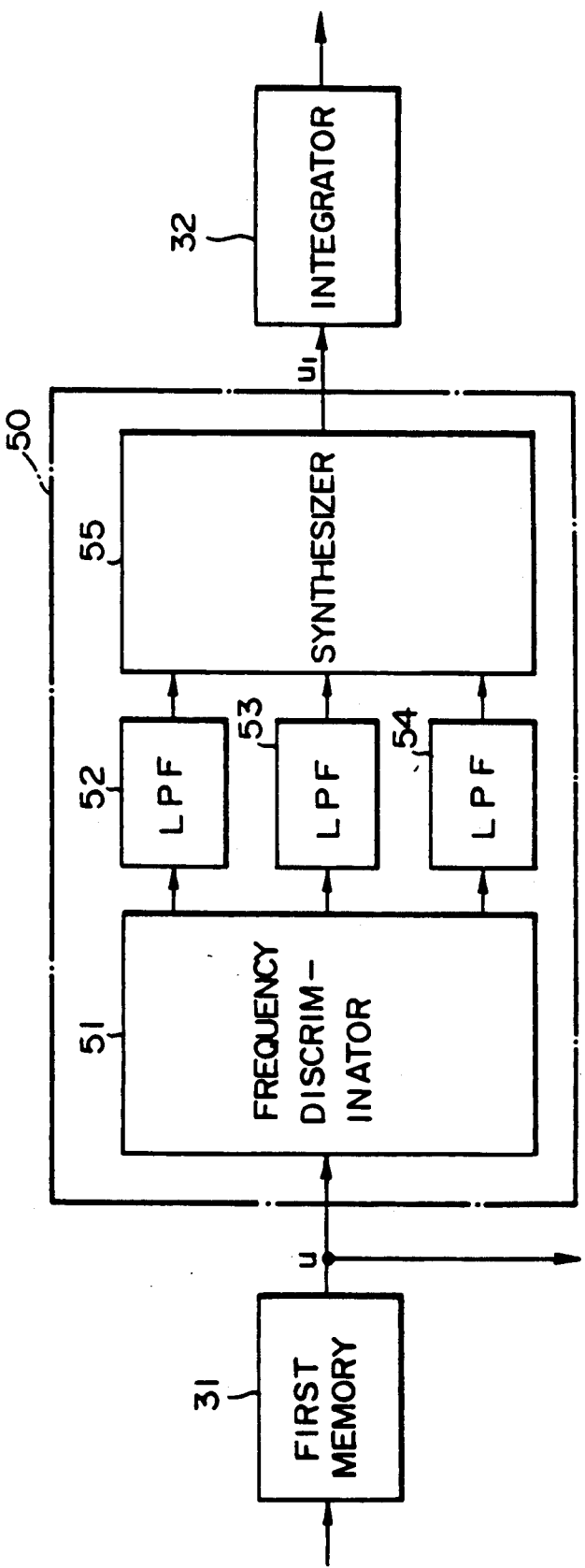

FIG. 13 shows such frequency processing circuits arranged in parallel. The data read out of the first memory 31 are first classified depending upon predetermined spatial frequencies by the frequency discriminator 51 of the three-dimensional compensation circuit 50.

In this embodiment, three frequency bands are discriminated, and low pass filters 52, 53 and 54 having different cut-off frequencies are arranged in parallel in correspondence with the respective frequency bands.

It goes without saying that the number of low pass filters and the number of frequencies discriminated may be selected as desired.

According to this embodiment, it is possible to process the return vortices from a small vortex to a large vortex on the x-z plane shown in FIG. 11 separately from each other and the optimum three-dimensional compensation of the spatial distribution of the components $u_2$ is enabled.

The three-dimensional compensation circuit 50 in FIG. 13 includes a synthesizer 55 for synthesizing the outputs of the low pass filters 52, 53 and 54, whereby it is possible to supply only the component $u_1$ with the component w removed to the integrator 32 for cumulative integration.

In the embodiments shown in FIGS. 12 and 13, only the integrator 32 shown in FIG. 4 is improved and the other structure is the same as that shown in FIG. 4, so that the total circuit structure is omitted.

As is clear from the above explanation, use of such Doppler velocities processed in advance enables the influence of the component w to be removed and velocity information containing very few error to be obtained in the same technique shown in the first embodiment.

The present invention having the above-described structure enables the measurement of the velocity of a flow by a Doppler method with easiness and at a low cost. It is possible to display the stream function and the streamline at real time from the thus-obtained velocity information, whereby it is possible to obtain a desired velocity distribution and the pressure distribution or the like in the closed region obtained from the velocity distribution.

What is claimed is:

1. A Doppler flow velocity measuring apparatus, comprising:

a means for obtaining a Doppler velocity distribution in the direction of a beam by utilizing a Doppler effect obtained from the echo reflected from a fluid when an ultrasonic wave or an electromagnetic wave is transmitted to and received from said fluid and scanning a desired transverse section with reflected echo;

a first memory means for storing the Doppler velocity distribution;

a means for obtaining a stream function by reading out the stored Doppler velocity in a direction orthogonal to the direction of said beam and cumulatively integrating said Doppler velocity at each point;

a second memory means for two-dimensionally storing said stream function obtained; and a means for obtaining the velocity component in the scanning plane which is orthogonal to the direction of said beam by reading out the stream function distribution in the direction of said beam and differentiating said stream function distribution in the direction of said beam.

2. A Doppler flow velocity measuring apparatus according to claim 1, wherein said direction in which said Doppler velocity is cumulatively integrated is the direction orthogonal to the direction of said beam.

3. A Doppler flow velocity measuring apparatus according to claim 1, wherein said Doppler velocity obtained from said reflected echo is the data subjected to compensation operation so as to remove the component in the direction orthogonal to said transverse section.

4. A Doppler flow velocity measuring apparatus according to claim 3, wherein said compensation operation includes a means for reading out Doppler velocity data in a direction different from the direction of said beam and cumulatively integrating said Doppler velocity data at each point, and a low pass filter for removing the high-frequency component of said data read out before the cumulative integration.

* * * * *